United States Patent
Williams et al.

(10) Patent No.: US 8,623,923 B2
(45) Date of Patent: Jan. 7, 2014

(54) PROCESS FOR THE PREPARATION OF AJOENE

(75) Inventors: David Michael Williams, Cardiff (GB); Robert Alun Saunders, Newport (GB); Gareth James Street Evans, Cardiff (GB)

(73) Assignee: Neem Biotech Limited, Cardiff, Wales (GB)

( * ) Notice: Subject to any disclaimer, the term of this patent is extended or adjusted under 35 U.S.C. 154(b) by 47 days.

(21) Appl. No.: 13/138,559

(22) PCT Filed: Mar. 2, 2010

(86) PCT No.: PCT/GB2010/050367
§ 371 (c)(1), (2), (4) Date: Sep. 2, 2011

(87) PCT Pub. No.: WO2010/100486
PCT Pub. Date: Sep. 10, 2010

(65) Prior Publication Data
US 2011/0319496 A1    Dec. 29, 2011

(30) Foreign Application Priority Data
Mar. 5, 2009 (GB) .................................. 0903869.6

(51) Int. Cl.
*A61K 31/105* (2006.01)
*C12P 11/00* (2006.01)

(52) U.S. Cl.
USPC ............. 514/707; 435/130; 568/22; 426/424; 426/601

(58) Field of Classification Search
USPC ............. 514/707; 568/22; 435/130; 426/424, 426/601
See application file for complete search history.

(56) References Cited

U.S. PATENT DOCUMENTS

| 4,643,994 A | 2/1987 | Block et al. |
| 5,612,077 A | 3/1997 | Hibi |
| 5,741,932 A | 4/1998 | Dressnandt et al. |

FOREIGN PATENT DOCUMENTS

| CN | 101156930 A | 4/2008 |
| CN | 101338329 A | 1/2009 |
| CN | 101928735 A | 12/2010 |
| RU | 2 239 630 C1 | 11/2004 |
| WO | WO 97/39115 A1 | 10/1997 |
| WO | WO 03/004668 A1 | 1/2003 |

OTHER PUBLICATIONS

E. Block et al., "Antithrombotic Organosulfur Compounds from Garlic: Strucural, Mechanistic, and Synthetic Studies," J of the Amer. Chem Soc., vol. 108, No. 22, Oct. 1986, pp. 7045-7055.
M. Casey et al., "Working Up The Reaction—Isolation of the crude product," Advanced Practical Organic Chemistry, Blackie, 1990, Sec. 9.3, pp. 145-146.
B.S. Furness et al., Vogel's Textbook of Practical Organic Chemistry, 1989, p. 158.
Iberl et al., "Products of Allicin Transformation: Ajoenes and Dithiins, Characterization and their Determination by HPLC*," Planta Medica 56, 1990, pp. 202-211.
Iberl et al., "Quantitative Determination of Allicin and Alliin form Garlic by HPLC*," Planta Medica 56, 1990, pp. 320-326.

*Primary Examiner* — Chih-Min Kam
(74) *Attorney, Agent, or Firm* — Pauley Petersen & Erickson

(57) ABSTRACT

A process for the preparation of ajoene, and of ajoene having a relatively high purity which may be obtained by the process. This invention also relates to processes for the preparation of allicin, and to a process for freeze concentrating allicin.

40 Claims, No Drawings

PROCESS FOR THE PREPARATION OF AJOENE

CROSS REFERENCE TO RELATED APPLICATION

This application is a 371 application of international application, PCT/GB2010/050367, filed on 2 Mar. 2010.

FIELD OF THE INVENTION

The present invention relates to a process for the preparation of ajoene, and to a composition comprising ajoene which may be obtained by the process. The present invention also relates to processes for the preparation of allicin, and to a process for freeze concentrating allicin.

BACKGROUND

Garlic has been used for millennia as a culinary herb and foodstuff. Further, many medical properties have been ascribed to garlic and it has been used in folk medicine for thousands of years.

Ajoene is a naturally occurring chemical compound which is derived from garlic. More particularly, ajoene is formed during the degradation of allicin, which is a chemically unstable, colourless to straw coloured oil which is thought to be responsible for much of the odour and biological activity of garlic. An intact garlic clove does not contain allicin but rather its odourless precursor alliin [(+) (S-allyl-L-cysteine sulfoxide)]. This is converted to allicin by a C—S-lyase present in the garlic plant termed alliinase. Alliin and alliinase are found in different compartments of the garlic clove and the cutting or crushing of the clove releases the enzyme allowing it to come into contact with alliin, which is converted to allicin. Allicin is both unstable and volatile, and will naturally degrade principally to diallyl disulphide, diallyl trisulphide, vinyl dithiins and ajoene. A method for preparing allicin in high yield and volume is described in WO-A-2003/004668, the entire contents of which are hereinby incorporated by reference.

Ajoene is presently of interest in a number of fields of endeavour, but predominantly in the medicinal field, including both human and animal pharmaceuticals. However, the study and hence the use of ajoene for such purposes has been curtailed since existing methods for producing ajoene have low selectively for ajoene. Consequently, ajoene is expensive to produce and then only in relatively small yields. For example, U.S. Pat. No. 5,612,077 describes a method using edible oil to produce a macerate containing mainly Z-ajoene but in small volumes and low concentration. U.S. Pat. No. 5,741,932 describes a method of preparing ajoene using cyclodextrin which is a complicated multi step method and which again produces small volumes at a low concentration.

Further, much of the previous research on garlic and its potential uses has not been specific about the active agent, which is typically referred to as 'a garlic extract' or 'garlic oil'.

Thus, there is a need for an improved process for obtaining ajoene in high yield, in high volumes, and at reasonable cost. There is also a need for an improved process for obtaining allicin, a precursor to ajoene, in high yield, in high volumes, and at reasonable cost.

SUMMARY OF INVENTION

According to a first aspect, the present invention is directed to a process for the preparation of ajoene, the process comprising a step of heating an acidic solution comprising allicin for a sufficient period of time such that at least a portion of the allicin is converted to ajoene.

In a second aspect, there is provided a composition comprising ajoene in an amount of at least about 30% w/v based on the total volume of the composition. The composition may be obtained by the process of the first aspect of the invention.

In a third aspect, there is provided a process for the preparation of allicin comprising: (i) mechanically treating a natural plant source of alliinase and simultaneously subjecting the mechanically treated product to centrifugal forces, thereby separating a solution comprising alliinase from the natural plant source of alliinase; and (i) contacting the solution comprising alliinase source with an aqueous solution of alliin, whereby the alliin is enzymatically converted to allicin by the alliinase in the solution comprising alliinase.

In a fourth aspect, there is provided a process for the preparation of allicin comprising oxidizing a solution comprising diallyl disulphide in the presence of potassium peroxomonosulphate at a temperature of from about 0° C. to about 30° C., followed by extraction of the resultant allicin into an organic solvent.

The process of the third and fourth aspects of the invention may be used to provide the solution comprising allicin which is converted to ajoene in the first aspect of the invention.

In accordance with a fifth aspect, there is provided a process for increasing the concentration of allicin in an aqueous solution of allicin, the process comprising freezing an aqueous solution of allicin, thereby increasing the concentration of allicin.

DETAILED DESCRIPTION OF THE INVENTION

Process for Preparing Ajoene

In accordance with the first aspect described above, the present invention is directed to a process for the preparation of ajoene, the process comprising a step of heating an acidic solution comprising allicin for a sufficient period of time such that at least a portion of the allicin is converted to ajoene.

The step of converting the allicin to ajoene comprises gently heating the acidic solution comprising allicin for a sufficient period of time such that at least a portion of the allicin is converted to ajoene. The temperature during the heating step is sufficient to cause the conversion of allicin to ajoene (which is a process by which two molecules of allicin are believed to condense to form one molecule of ajoene, together with other compounds such as vinyl dithiin). The heating step may be carried out at a temperature of from about room temperature to about 80° C. For example, the heating step may be carried out at a temperature of from about 30° C. to about 80° C., for example, about 40° C. to about 70° C. The heating step may be carried out at temperature of from about 35° C. to about 45° C., or from about 40° C. to about 50° C., or from about 45° C. to about 55° C., or from about 50° C. to about 60° C., or from about 55° C. to about 65° C. In embodiments, the heating step is carried out at a temperature of about 30° C., or about 40° C., or about 50° C., or about 60° C. Generally, the solution comprising allicin is slowly stirred during heating for a sufficient period of time until the reaction is complete or the desired level of conversion has been obtained. The extent of conversion from allicin to ajoene may be monitored, for example, by HPLC using the methods outlined below and by monitoring the UV absorption spectrum of allicin and/or ajoene. Generally, the higher the temperature, the shorter the period of time required to convert the allicin to ajoene. The heating step may be conducted for a period of time of about 1 to about 10 hours, for example, from about 3 to 8 hours. In embodiments, the heating step is conducted for about 4 hours, or for about 4.5 hours, or for about 5 hours, or for about 5.5 hours, or for about 6 hours, or for about 6.5 hours, of for about 7 hours.

In an embodiment, a majority of the allicin is converted to ajoene. By majority is meant at least 50% of the allicin in the starting solution is converted to ajoene, as may be determined by the HPLC methods outlined below. For example, the heating step may be conducted until at least about 60%, or at least about 70%, or at least about 80%, or at least about 90% of the allicin in the starting solution is converted to ajoene.

Advantageously, substantially all of the allicin is converted to ajoene. By substantially all is meant that the heating step is continued until no further ajoene is detected using the HPLC methods outlined below.

The solution during the heating step may be gently agitated, for example by slow stirring, to cause the constituents to mix. The degree of agitation is preferably controlled in order to prevent the formation of an emulsion. For example, if an emulsion begins to form, the extent of agitation may be reduced (i.e., to a less severe level of agitation) or even stopped until any emulsion has cleared.

The process may further comprise removing the organic solvent, for example under vacuum, to obtain an oily fraction comprising ajoene in an amount of at least about 30% w/v based on the total volume of the oily fraction, (i.e., grams of ajoene per liter of liquid in the oily fraction).

The solution containing ajoene may be filtered prior to removing the solvent to remove any residual solid material. For example, the solution containing ajoene may be filtered through a 30 cm 113 Whatman paper filter.

In an embodiment, the freshly converted solution containing ajoene is partitioned using an aqueous alcohol solution and a non polar alkane solvent such, as pentane, in a ratio ranging from (1:1 or 2:1 by volume). This treatment removes any non polar allicin metabolites such as the polysulphides and vinylditihins.

In an embodiment, the solvent is reduced under vacuum at a temperature between about 40 to 80° C., preferably at about 50° C. This produces an aqueous solution and insoluble syrup. The acid used in the conversion step may be neutralised by drop-wise addition of a base, for example, a strong base such as sodium hydroxide. The solution and syrup are then extracted with an ether such as methyl tert butyl ether (TBME) in a ratio of from about 2:1 to about 1:1 by volume. The extraction can be performed up to 3 times to ensure complete extraction.

The solution comprising allicin may contain at least about 2,000 ppm allicin, for example at least about 5,000 ppm allicin, for example at least about 7,000 ppm allicin, for example at least about 10,000 ppm allicin. Advantageously, the solution comprising allicin may contain at least about 15,000 ppm allicin, for example at least about 17,000 ppm, or for example at least about 20,000 ppm. The solution typically comprises less than about 25,000 ppm allicin, for example less than about 22,000 ppm allicin.

As noted below, the allicin in the solution comprising allicin may be derived from garlic, which may be hard-necked or soft-necked. Varieties of hard-necked garlic include Rocambole, Porcelain, Purple Stripe (sometimes referred to as 'Purple Streak)', Marbled Purple Stripe, Glazed Purple Stripe, Pure White and Pearl white. Varieties of soft-necked garlic include Artichoke, Asiatic, Turban, Silverskin and Silverskin Creole. Advantageously, the allicin is derived from hard-necked garlic, such as for example, Pure White or Pearl White (e.g., Pure White or Pearl White garlic obtained from the Tiashan region of China). The yield of ajoene when the allicin in the acidic solution of allicin which is heated and converted to ajoene is derived from hard-necked garlic has been found to be significantly improved (of the order of 20-25% increase in yield) compared to conversion in a non-acidic solution.

The solution comprising allicin, which is converted to ajoene, is an acidic solution. The pH of the solution comprising allicin may be about 5 or less, or less than 5. Advantageously, the pH of the solution comprising allicin is from about 3 to about 5, or from about 3 to less than 5, or from about 3 to about 4. The pH of the solution may be greater than about 2. In embodiments, the pH of the solution comprising allicin is about 3, or about 4, or about 5.

The solution comprising allicin may be acidified to a desired pH by addition of an appropriate amount of a suitable acid. Allicin in solution typically has a slightly acid pH. Thus, an appropriate amount of acid is an amount which causes the pH of the solution comprising allicin to fall to the desired pH.

The acid may be any suitable organic acid or an inorganic acid. In an embodiment, the acid is a strong acid having a $pK_a$ of less than about 5. The acid may be one or more acid selected from the group consisting of acetic acid, phosphoric acid, sulfuric acid and hydrochloric acid. The amount of acid in the solution may be from about 0.1 to 5% (v/v). In an embodiment, the amount of acid in the solution is about 1% (v/v). Advantageously, the acid is acetic acid, for example, glacial acetic acid. This acid is relatively volatile and can therefore be readily removed from the solution after the conversion step has been completed.

In a particularly advantageous embodiment, the solution of allicin comprises acetic acid, preferably glacial acetic acid, in amount of 1 part glacial acetic acid to 100 parts of solution and has a pH of about 4. The solution further comprises acetone and water.

Whilst not wishing to be bound by theory, it is believed that the acid facilitates the conversion of allicin to ajoene as a proton donor. The acidic conditions, advantageously at a pH of about 3 to about 5, or from about 3 to less than 5, leads to a much cleaner ajoene product which comprises less impurities such as diallyl disulphide and higher polysulfides.

The solution comprising allicin advantageously comprises a solvent that is suitable for solvating ajoene. Suitable solvents are alcohols, ethers and ketones. Preferred alcohols include methanol, ethanol and propanol. In one embodiment, the solvent is acetone. In another embodiment, the solvent is butanol. In another embodiment, the solvent is butanone. In another embodiment, the organic solvent has a boiling point less than about 100° C., for example less than about 90° C., for example less than about 80° C., for example less than about 70° C., for example less than about 60° C. The amount of organic solvent may be from about 40 to 70% (v/v) with the balance water and acid.

Ajoene exists in two isomer forms (cis (Z) and trans (E)), and will typically be isolated as a mixture of both isomers. However, the solvent may be selected depending on the Z:E ratio of the ajoene required. Acetone typically results in a product comprising Z and E isomers in a ratio of about 1:3, whilst butanol as solvent may be used to obtain a product having a Z:E ratio greater than about 4:1.

The solution comprising allicin and acid may comprise, consist of or consist essentially of allicin, acid, organic solvent and water.

In an embodiment, the heating step of the process of the first aspect of the invention is conducted in the absence of oil such as, for example, edible oil.

The process of the first aspect of the invention enables the production and isolation of ajoene in high yield, and in amounts up to about eight times the amount which can be produced from garlic alone using existing production methods. The maximum theoretical yield is one molecule of ajoene for two molecules of allicin. Typical yields obtained by the present process are approximately one molecule of ajoene for every four molecules of allicin.

The present process also enables the production and isolation of ajoene in relatively high volumes. Further, the present process enables the production and isolation of ajoene in relatively high concentrations and purity.

By high purity, we mean that the oily fraction produced after the solvent is removed comprises ajoene in an amount of at least about 30% by weight per volume (w/v) of liquid in the oily fraction. In embodiments, the oily fraction comprises 35% w/v ajoene, for example at least about 40% w/v ajoene, for example at least about 45% w/v ajoene, for example at least about 50% w/v ajoene.

The process may further comprise drying, for example using magnesium sulphate, the oily fraction comprising ajoene and suspending the dried oily residue in edible oil to form an edible oil macerate containing up to about 5% ajoene by weight/volume based on the total volume of the oil macerate. In an embodiment, the oil macerate contains up to about 4% by weight/volume ajoene. The edible oil may be vegetable oil, animal oil or fat, hydrogenated vegetable oil or animal fat or synthetic oil or fat. Liquid oil is preferably used, for example, olive oil. In an embodiment, the edible is olive oil and the macerate contains up to about 4% ajoene (w/v).

The edible oil macerate can be further diluted with a suitable oil for use to between 100 ppm and 500 ppm ajoene depending on the end user and application. This product may be stable for a minimum of 2 years when suitably encapsulated and used, for example, as a health food supplement or other application.

Further purification of the ajoene obtained can be achieved by a further step of suspending the oil residue in an organic polar solvent, for example diethyl ether, and partitioning against water which results in the removal of non-polar compounds, typically in the form of polysulfides.

Any residual acid may be neutralised by the addition (e.g., drop-wise) of a suitable amount of base such as, for example, sodium hydroxide.

At any stage during the process the various solutions may be filtered and/or centrifuged to remove solid deposits, such as plant debris comprised in the original allicin solution.

Process for Preparing Allicin

In an embodiment of the first aspect of the present invention, and in accordance with the third aspect of the present invention, the solution comprising allicin is provided by a method comprising i) mechanically treating a natural plant source of alliinase and simultaneously subjecting the mechanically treated product to centrifugal forces, thereby separating a solution comprising alliinase from the natural plant source of alliinase; and ii) contacting the solution comprising alliinase source with an aqueous solution of alliin, whereby the alliin is enzymatically converted to allicin by the alliinase in the solution comprising alliinase.

In an embodiment step (i) is conducted in a centrifugal juicer, and step (ii) may be carried out simultaneously with at least a part of step (i). Centrifugal juicers, also known as centrifugal juice extractors, typically comprise a basket which can be spun at a high rate. The basket has teeth that grinds the natural plant source of alliinase (e.g., garlic cloves, which may be peeled or unpeeled) into a soft mush or pulp. Since the basket is spinning at a high rate the pulp is thrown against the side of the basket. The side of the basket is porous, therefore allowing the liquid in the pulp to be separated from the pulp using centrifugal force. The liquid solution (comprising alliinase) is collected and can then be contacted with the alliin solution. An example of a suitable centrifugal juicer is a JE700 Proline® Domestic Juicer. It will be appreciated by those skilled in the art that some solid material may pass through the pores during separation. Any solid material can be removed from the alliinase solution by any suitable method, such as filtration and/or centrifuge. The use of a centrifugal juicer has surprisingly been found to offer advantages over existing methods. First, the rapid separation of the solid plant material from the liquid constituent of the natural plant source of alliinase enables greater temperature control of the alliinase prior to and during its conversion to allicin, and also means that the alliinase in the liquid constituent is able to be contacted with the aqueous alliin solution very quickly, typically within about 5-30 seconds of the mechanical treatment, for example between about 10-20 seconds, or within about 10 seconds of the mechanical treatment. In the prior art blending method in WO-A-2003/004668, whilst able to produce at that time allicin at levels not previously achievable, the raw material being blended (i.e., garlic) was blended over relatively much longer periods (i.e., in the order of minutes) which resulted in an increase in temperature (typically raising the temperature of the alliinase containing solution to about 35° C.). In contrast, the much quicker treatment of the raw material using a centrifugal juicer means there is little or no increase in temperature. Consequently, the alliinase in the resultant solution is less prone to degradation, and also the addition of the alliinase solution to the alliin solution will generally not lead to any significant increase in temperature, which in turn will mean the formed allicin will also be less prone to degradation. Further, the decrease in time between the production of the alliinase solution and contacting with the alliin solution means there is less time for the alliinase to cause the conversion of alliin naturally produced during the treatment step. The result is a much more efficient process which leads to the production of allicin in volume and purity as least as good as and preferably greater than the methods described in WO-A-2003/004668, with the additional advantage of much reduced reaction times due to the rapid separation of the alliinase solution from the natural plant source of alliinase.

In a preferred embodiment, the natural plant source of alliinase is treated in accordance with steps (i) and (ii) and is simultaneously contacted with the aqueous solution of alliin. Thus, the process is conducted continuously with fresh natural plant source of alliinase being juiced as the solution comprising alliinase is fed to a reactor containing the aqueous solution of alliin.

The natural plant source of alliinase used in the processes of the present invention may be obtained from an allium genus plant, typically the bulbous portion thereof. Most preferably it is garlic, Allium Sativum which is readily available and cheap and which has a relatively high concentration of alliinase. The garlic may be hard-necked or soft-necked. Varieties of hard-necked garlic include Rocambole, Porcelain, Purple Stripe (sometimes referred to as 'Purple Streak)', Marbled Purple Stripe, Glazed Purple Stripe, Pure White and Pearl white. Varieties of soft-necked garlic include Artichoke, Asiatic, Turban, Silverskin and Silverskin Creole. Advantageously, the allicin is derived from hard-necked garlic, such as for example, Pure White or Pearl White (e.g., Pure White or Pearl White garlic obtained from the Tiashan region of China). The yield of ajoene when the allicin in the acidic solution of allicin which is heated and converted to ajoene is derived from hard-necked garlic has been found to be significantly improved (of the order of 20-25% increase in yield) compared to conversion in a non-acidic solution.

As will be understood by a person skilled in the art, the quality of the garlic in terms of alliinase may vary with the time of year and the local environment in which the garlic is produced. The skilled person will therefore be able to conduct straight forward preliminary tests to establish the quality of any given source of garlic and determine its suitability for processing in accordance with the present invention to produce allicin and ajoene.

The raw garlic is typically in the form of bulbs and/or cloves which may be treated in unpeeled or peeled state. Preferably the raw garlic is peeled and cleaned prior to being mechanically treated in the centrifugal juicer.

After the contacting step the solution comprising the alliinase and alliin is stirred for about 1 to 6 hours, for example, for about 2-4 hours, or until the desired level of conversion of alliinase and alliin to allicin has been achieved. The temperature during stirring is preferably maintained at about 30° C. The extent of conversion to allicin may be monitored, for example, by HPLC using the methods outlined below and by monitoring the UV absorption spectrum of allicin. As will be appreciated by persons skilled in the art, the final concentration of allicin may vary depending on the amount and type of raw garlic. The final solution may comprise at least about 2,000 ppm allicin, for example at least about 5000 ppm allicin, for example at least about 10,000 ppm allicin, or at least about 12,000 ppm allicin, or at least about 15,000 ppm allicin, or at least about 17,000 ppm, or at least about 20,000 ppm allicin.

The resultant allicin rich aqueous solution, typically comprising between about 10,000 and 22,000 ppm, is preferably clarified prior to conversion to ajoene. The clarification process may involve sedimentation at low temperature, centrifugation, filtration, and/or addition of salt, or a combination thereof, to precipitate and remove any protein, fibre and other plant debris from the solution. This clarification process generally improves the overall process of converting the allicin to ajoene and any subsequent purifying steps.

For example, the allicin rich solution may be left to sediment at low temperature, for example below 5° C., for a sufficient period of time, for example, about 1-3 days, or for example about 2 days. Following which the clear supernatant liquid is removed, for example, by decantation. Any residual liquid can be removed from the sediment by centrifugation and then combined with the supernatant liquid. The temperature is preferably maintained below 5° C. throughout the process. The clarified supernatant solution comprising allicin may be filtered.

Prior to conversion to ajoene, the clarified allicin solution is preferably extracted into an organic solvent, such as acetone. The organic solvent is preferably chilled to a temperature of less than 0° C. The two liquids are stirred for a period of time to ensure homogenisation. The temperature is preferably kept at or below 5° C. at all times. The aqueous acetone solution may then be left to sediment for a further period of time, for example, 24 hours, at a temperature of below 5° C., for example, below 0° C., or below −5° C., or below about −10° C., and sediment removed. The solution may then be salted by the addition of suitable salt, for example, sodium chloride, followed by stirring of the mixture, after which the solutions is allowed to stand, at a temperature of less than 10° C., for a sufficient time for the organic solvent layer comprising allicin to separate from the brine layer. The degree of agitation is preferably controlled in order to prevent the formation of an emulsion. For example, if an emulsion begins to form, the extent of agitation may be reduced (i.e., to a less severe level of agitation) or even stopped until any emulsion has cleared. Alternatively, the emulsion can be removed and centrifuged to cause the two phases to separate into two layers which are then decanted and returned to the mother solution.

The extraction steps may be repeated two or three times. For extracting the allicin from the aqueous phase into a solvent phase a ratio of aqueous phase to solvent of from about 1:1 to about 2:1 (v/v) is suitable. It is the organic layer comprising allicin that may be used in the heating step of the process of the first aspect of the invention.

The salt may be an inorganic salt, such as sodium chloride, ammonium chloride or ammonium sulphate. In one embodiment, the salt is sodium chloride.

In a preferred embodiment, the salt is sodium chloride and the organic solvent is acetone.

At any stage during the process, the allicin rich solvent layer may be further purified by drying, sedimentation, filtering and/or cryogenic treatment to remove any remaining plant matter, prior to a heating step to convert the allicin to ajoene.

For example, the organic solvent layer comprising allicin, prior to heating to convert the allicin to ajoene, may be dried, for example with magnesium sulphate, and filtered, for example, through celite.

The composition of the allicin solvent extract may then be modified with the addition of further solvent or solvents to optimise the conditions for the conversion of allicin to ajoene. Suitable solvents are those described above. The allicin extract is then mixed with acid and optionally water in accordance with the procedures described above, and then subjected to heating to convert the allicin to ajoene.

As noted above, the solvent(s) may be selected depending on the Z:E ratio of the ajoene required. Acetone typically results in a product comprising Z and E isomers in a ratio of about 1:3, whilst butanol as solvent may be used to obtain a product having a Z:E ratio greater than about 4:1.

Thus, the high volume and purity of ajoene produced in accordance with the present invention is based, at least in part, on the improved method of production of allicin described above.

Alternatively, the allicin may be stored for other purposes. Allicin is extremely unstable in water at concentrations above about 5000 ppm. However, allicin is stable at a concentration of up to about 5000 ppm at −40° C. provided the solution has been filtered to remove impurities. Further, the stability of the allicin can be increased in the presence of a slightly acidic solution. After extraction with a solvent such as diethyl ether, and without dilution, the allicin must be kept at or below −70° C. since breakdown of the allicin product begins immediately. Therefore, depending on the concentration of the final solution of allicin, steps may be taken to dilute the allicin solution for storage. Therefore, it is preferable to dilute the allicin, in order to increase its stability, as quickly as possible. For example, the solution may be diluted to less than about 500 ppm, for example less than about 150 ppm. The diluted solution may be further stabilized by adjusting the pH using a suitable buffer, such as citric acid.

The stability of allicin may be increased further by removing substantially all protein, garlic debris and other solid materials. In this form allicin can be stored at relatively high concentration levels for lengthy periods at low temperatures of about 0° C. or below. Thus, there is provided a method of treating and storing allicin at a concentration of at least 5000 ppm, the method comprising treating an aqueous solution of allicin having a concentration of at least about 5000 ppm to remove substantially all protein, garlic debris and any other solid material, and storing the aqueous solution of allicin at a temperature of about 0° C. or below. The treated aqueous solution of allicin may be stored for a period of up to about 2 months at −10° C. without degradation of the allicin. The aqueous solution of allicin may be prepared in accordance with the third aspect of the invention describe above.

In accordance with a fifth aspect, there is provided a process for increasing the concentration of allicin in an aqueous solution of allicin, the process comprising freezing an aqueous solution of allicin, thereby increasing the concentration of allicin. The aqueous solution of allicin may be prepared in accordance with the third aspect of the invention described above. The aqueous solution of allicin is preferably clarified in accordance with the methods described above prior to freezing. For example, the aqueous solution of allicin rich solution may be left to sediment at low temperature, for example below 5° C., for a sufficient period of time, for example, about 1-3 days, or for example about 2 days. Following which the clear supernatant liquid is removed, for example, by decantation. Any residual liquid can be removed from the sediment by centrifugation and then combined with the supernatant liquid. The temperature is preferably maintained below 5° C. throughout the process. The clarified supernatant solution comprising allicin may be filtered.

The freezing may be effected by slow cooling the aqueous solution of allicin to a temperature of −10° C. or below over a period of time of from about 1 to about 3 days, for example, for about 2 days. The slow cooling means the solution freezes gradually from the outside of the solution towards the centre. The freezing process is advantageously continued until about 50% by volume of the solution of allicin is frozen. This has the effect of increasing the concentration of allicin in the remaining liquid portion.

The process may further comprise mechanical treating the frozen aqueous allicin to produce a liquid/slush, and filtering the liquid slush under vacuum at a temperature of less than about 15° C. to produce a relatively viscous solution of allicin (relative to the viscosity of the aqueous solution of allicin prior to freezing) having an increased allicin concentration. The liquid/slush may be stirred during filtering to aid the filtering process. The concentration of allicin in the viscous solution may be increased by up to about 50% compared to the concentration of allicin in the aqueous solution of allicin prior to freezing. The concentration of allicin in the viscous solution may be increased by at least about 10% compared to the concentration of allicin in the aqueous solution of allicin prior to freezing.

The viscous solution of allicin, or at least a portion thereof, may be treated in accordance with the first aspect of the invention and converted to ajoene.

In accordance with an alternative embodiment of the first aspect of the present invention, and in accordance with a fourth aspect of the present invention, the solution comprising allicin is provided by a method comprising oxidizing a solution comprising diallyl disulphide in the presence of potassium peroxomonosulphate at a temperature of between about 0° C. and 30° C., followed by extraction of the resultant allicin into an organic solvent. In one embodiment, the temperature is equal to or less than about 10° C., for example about 5° C.

The amount of diallyl disulphide and potassium peroxomonosulphate may be sufficient to produce an aqueous solution of allicin having a concentration of from about 2000 to about 22,000 ppm. For example, the amount of diallyl disulphide and potassium peroxomonosulphate may be sufficient to produce an aqueous solution of allicin having a concentration of from about 5,000 ppm, or about 7,000 ppm, or about 10,0000 ppm, or about 12,000 ppm, or about 15,000 ppm or about 17,000 ppm, or about 20,000 ppm.

The total amount of potassium peroxomonosulphate is advantageously added gradually to the solution of diallyl disulphide over a period of time, for example, about 2 hours with stirring.

Methods for preparing allicin synthetically from diallyl disulphide are known [e.g., Cavallito. C. J. Bailey, J. H., J. Am. Chem. Soc. 66, (1944). 1950-1951; Small, L. V. D., Bailey, J. H., Cavallito C. J., J. Am. Chem. Soc. 69, (1947), 1710-1713)]. In these methods, hydrogen peroxide is the oxidizing agent. These methods also require the use of volatile and low boiling point solvents, such as ether, and there are safety issues with the use of large volumes of such solvents, which the present method negates.

Ajoene

The present invention is directed to a composition comprising ajoene in an amount of least about 30% by weight per volume (w/v) of liquid in the composition. The composition may be obtained by a process according to the first aspect of the invention. In embodiments, the composition comprises 35% w/v ajoene, for example at least about 40% w/v ajoene, for example at least about 45% w/v ajoene, for example at least about 50% w/v ajoene.

The present invention is directed to a an edible oil macerate containing up to about 5% ajoene by w/v based on the total volume of the oil macerate produced. The macerated may be obtained by suspending sufficient ajoene concentrate in oil to produce the required concentration. In an embodiment, the oil macerate contains up to about 4% by volume/volume ajoene. The edible oil may be any suitable vegetable oil. The edible oil may be vegetable oil, animal oil or fat, hydrogenated vegetable oil or animal fat or synthetic oil or fat. Liquid oil is preferably used, for example, olive oil. In one embodiment, the edible oil is olive oil.

The present invention thereby enables the production of ajoene in bulk quantities via a commercially viable process. For example, the process enables the production of ajoene in kilogram amounts. As such, the present invention is also directed to ajoene prepared on a kilogram scale.

The process according to the invention provides the pharmacologically active substance ajoene in amounts which make it possible to prepare a commercial product containing a standardize amount of ajoene.

The ajoene prepared according to the invention is suitable for any of the known and proposed uses. It stability allows for it to be used for the preparation of standardized pharmaceuticals, neutraceuticals, animal feed additives and in cosmetic applications. Particularly for cardiovascular disorders such as, for example arteriosclerosis, thrombotic events, high blood pressure inter alia, and for various bacterial infections, fungal infections and a remedy for some organic and metabolic disturbances. As a preventive health remedy it can also be used in the food additive sector.

For the avoidance of doubt, the present application relates to the subject-matter described in the following numbered paragraphs:

1. A process for the preparation of ajoene comprising: (a) providing a solution comprising allicin; (b) increasing the salt concentration of the solution comprising allicin and extracting the allicin into an organic solvent, thereby forming a solvent layer comprising allicin and a brine layer; (c) optionally separating the solvent layer and the brine layer; and (d) converting the allicin to ajoene.

2. A process according to paragraph 1, where step d) comprises heating the allicin at a temperature between room temperature and the boiling point of the organic solvent into which the allicin is extracted for a period of from about 1 to about 5 hours.

3. A process according to paragraph 1 or 2, further comprising separating the solvent layer and the brine layer if step (c) of claim 1 is not performed prior to heating step (d), and removing the organic solvent to produce an oily fraction comprising ajoene in an amount of at least about 30% w/v based on the total volume of the oily fraction.

4. A process according to paragraph 3, wherein the oily fraction is extracted with an organic polar solvent to remove residual organic solvent and dried to remove residual water.

5. A process according to paragraph 3 or 4, further comprising suspending the oily fraction in edible oil to form an oil macerate containing about 4-5% w/v ajoene based on the total volume of the oil macerate.

6. A process according to any preceding paragraph, wherein the organic solvent in step (b) is selected from alcohols, ethers and ketones.

7. A process according to paragraph 6, wherein the solvent is acetone, butinol or butinone.

8. A process according to any preceding paragraph, wherein the salt is sodium chloride.

9. A process according to paragraph 4, wherein the organic polar solvent is diethyl ether.

10. A process according to any preceding paragraph, wherein prior to step (d) the solvent layer comprising allicin is filtered and/or centrifuged.

11. A process according to any preceding paragraph, wherein step b) comprises the addition of salt over a period of up to about 2 hours, followed by the addition of the organic solvent over a period of up to about 2 hours, and wherein the temperature of the solution is maintained between about 0° C. and 50° C.

12. A process according to any of paragraph 1-10, wherein step b) comprises the addition of the organic solvent with over a period of up to about 2 hours, followed by the addition of salt over a period of up to about 2 hours, and wherein the temperature of the solution is maintained between about 0° C. and 50° C.

13. A process according to any preceding paragraph, wherein the salt and organic solvent are added to the solution comprising allicin with agitation, and wherein the formation of an emulsion during addition of the salt and organic solvent is prevented.

14. A process according to any one of paragraphs 11-12, wherein the salt is sodium chloride and the organic solvent is acetone, and wherein step d) comprises heating the allicin at a temperature of about 50-55° C. for a period of about 3-5 hours, preferably about 4 hours.

15. A process according to any preceding paragraph, wherein step a) comprises:
i) mechanically treating a natural plant source of alliinase and simultaneously subjecting the mechanically treated product to centrifugal forces, thereby separating a solution comprising alliinase from the natural plant source of alliinase; and
ii) contacting the solution comprising alliinase source with an aqueous solution of alliin, whereby the alliin is enzymatically converted to allicin by the alliinase in the solution comprising alliinase.

16. A process according to paragraph 15, wherein step (i) is conducted in a centrifugal juicer.

17. A process according to paragraph 15 or 16, wherein step (ii) is carried out simultaneously with at least a part of step (i).

18. A process according to any one of paragraphs 15-17, wherein after the contacting step the solution comprising alliin, alliinase and allicin is stirred for about 1 to 3 hours.

19. A process for the preparation of allicin comprising: (a) mechanically treating a natural plant source of alliinase and simultaneously subjecting the mechanically treated product to centrifugal forces, thereby separating a solution comprising alliinase from the natural plant source of alliinase; and (b) contacting the solution comprising alliinase source with an aqueous solution of alliin, whereby the alliin is enzymatically converted to allicin by the alliinase in the solution comprising alliinase.

20. A process according to paragraph 19, wherein step (i) is conducted in a centrifugal juicer.

21. A process according to any preceding paragraph, wherein the natural plant source of alliinase is raw garlic.

22. A process according to paragraph 21, wherein the raw garlic is in the form of bulbs of cloves which preferably have been peeled and cleaned.

23. A process according to any preceding paragraph, wherein the solution comprising allicin contains at least about 5000 ppm allicin 24. A process according to any preceding paragraph, wherein the solution comprising allicin contains at least about 10,000 ppm allicin.

25. A process according to any preceding paragraph, wherein the solution comprising allicin contains at least about 12,000 ppm allicin.

26. A process according to any preceding paragraph, wherein the solution comprising allicin contains at least about 15,000 ppm allicin.

27. A process according to any one of paragraphs 1-14, wherein step a) comprises oxidizing a solution comprising diallyl disulphide in the presence of potassium peroxomonosulphate at a temperature of from about 0° C. to about 30° C., followed by extraction of the resultant allicin into an organic solvent.

28. A process for the preparation of allicin comprising oxidizing a solution comprising diallyl disulphide in the presence of potassium peroxomonosulphate at a temperature of from about 0° C. to about 30° C., followed by extraction of the resultant allicin into an organic solvent.

29. A process according to paragraph 27 or 28, wherein the amount of diallyl disulphide and potassium peroxomonosulphate is sufficient to produce an aqueous solution of allicin having a concentration of from about 5000 ppm to about 20,000 ppm.

30. A process according to any one of paragraphs 27-29, wherein the temperature is equal to or less than about 10° C.

31. A process according to any one of paragraphs 27-30, wherein the total amount of potassium peroxomonosulphate is added gradually to the solution of diallyl sulphide over a period of about 2 hours.

32. A composition comprising at least about 30% w/v ajoene based on the total volume of the composition, obtainable by a method according to any one of paragraphs 1-17, 20-26 and 28-30.

33. A composition according to paragraph 31 comprising at least about 35% w/v ajoene.

34. A composition according to paragraph 32 comprising at least about 40% w/v ajoene.

35. A composition according to paragraph 33 comprising at least about 45% w/v ajoene.

36. A composition according to paragraph 34 comprising at least about 50% w/v ajoene.

The invention will now be described by way of example only and without limitation with reference to the following examples.

EXAMPLES

Reverse Phase HPLC Methods
  Determination of Allicin Concentration (Calibration via a Standard Allicin Solution)
    Peak identification: allicin @ 9.5 minutes
    Column: Ace 5 C18; Dimensions: 250×4.6 mm
    Guard Column: Ace 5 C18
    Mobile phase: 50% methanol-50% water
    Temperature: 30° C.
    Detection wave length: 210 nm (UV)
    Sample volume: 20 µL
    Sample solvent: water
    Flow rate: 1.0 ml/min
  Determination of Ajoene Concentration (Calibration Via a Standard Ajoene Solution)
    Peak identification: ajoene (both E/Z eluted together) @ 11.1 minutes
    Column used: ACE 5 C18; Dimensions: 250×4.6 mm
    Guard Column: Ace 5 C18)
    Mobile phase: Solvent A water-Solvent B methanol
    Flow rate: 1.0 ml/min
    Gradient:

| Min | % Solvent B |
|---|---|
| 0 | 50 |
| 15 | 100 |
| 20 | 100 |
| 20.0 | 150 |
| 25 | 50 |

Temperature: 30° C.
  Detection wave length: 254 nm*UV)
  Sample volume: 20 µL
  Sample solvent: Methanol
  Normal Phase Method for the Determination of Ajoene E and Z Isomers (Calibration via a Standard Ajoene Solution)
    Peak identification: Zajoene @ 14 minutes; E ajoene @ 17 minutes
    Column used: Silica; Dimensions: 250×4.6 mm, manufactured by NN Scientific Ltd.
    Mobile phase: 92% Hexane-8% 2-Propanol
    Temperature: 30° C.
    Detection wavelength: 240 nm (UV)
    Sample volume: 20 µL
    Sample solvent: 2-Propanol
    Flow rate: 1.0 ml/min

Example 1

5 liters of alliinase rich garlic juice extract prepared using a centrifugal juicer (JE700 Proline® Domestic Juicer extractor), was blended with 35 liters of 10% Alliin solution in a reactor and stirred for 3 hours. The garlic was a pre peeled Spanish white variety obtained from the local market. The reaction temperature was maintained at 30° C. with a water jacket. Reaction completion was determined by HPLC using the method described above. The resulting 40 liter solution was determined to have an allicin concentration of 15,000 ppm. The 40 liters of allicin solution was left to sediment at 4° C. for 48 hours. The clear supernatant was decanted off. The liquid from the remaining sediment was removed by centrifuging at 3000 rpm for 30 minutes at 0° C. and was combined with the supernatant. The clarified solution was filtered though a Whatman 113 filter paper then placed in a 100 liters reactor. 40 liters of Ice-cold Acetone was added to the reactor and the two liquids were stirred for 2 hours to ensure total homogenisation. The temperature was kept below 5° C. at all times. The aqueous acetone solution was then left to sediment for 24 hours at −10° C. Any sediment was decanted off. 15 kg of sodium chloride was added to the clarified solution and the mixture was stirred for 3 hours in a baffled reactor. The solution was allowed to stand for 12 hours and cooled to less than 10° C., which was sufficient time for the immiscible acetone layer to separate from the brine layer. The allicin concentration of the top acetone layer and the bottom brine layer was determined to be 3% (w/v) and 0.1% (w/V) respectively.

The acetone layer was dried with magnesium sulphate and filtered through celite. This left 25 liters of acetone. The acetone layer was then mixed with a 25 liter solution of acetone/water/acetic acid (65/34/1 (v/v)) in a 100 liters reactor. The solution was then heated at 60 degrees for 5 hours. The reaction was monitored by the HPLC ajoene method described above. The reaction mixture was then paper filtered through a 30 cm 113 Whatman paper filter. The filtrate was then reduced under vacuum at 50° C. to remove solvent. The residue was centrifuged at 2000 ppm for 5 minutes. The sediment liquid was placed in a separating funnel and the bottom oil was removed. The oil was reduced under vacuum at 80° C. degrees to remove any residual solvent. A total of 275 g of oil was obtained the ajoene content was determined to be 35% (w/v) and the E/Z ratio was determined to be 3:1 by HPLC (as described above).

Example 2

The procedure described in Example 1 was used to produce 30 liters of a 15,000 ppm allicin solution. The liquid was left to sediment for 48 hours then filtered through celite under vacuum. The clarified solution was then mixed with 11 Kg of sodium chloride in a 100 liters reactor. The reactor was cooled at −10° C. for 24 hours. The liquid was then filtered through paper to remove protein, fibre and excess salt. The liquid was transferred to a 100 liters reactor. 30 liters of ice-cold acetone was added to the reactor, the liquids were stirred slowly with an impeller designed to ensure enough turbulence to allow transfer of the allicin from the aqueous layer to the organic layer without generating excess emulsion. The solution was allowed to stand for 12 hours and cooled to less than 10° C.; this was sufficient time for the immiscible acetone layer to separate from the brine layer. Approximately 10 liters of emulsion was generated at the interface of the bi-layer. This emulsion was broken in a centrifuge at 3000 rpm for 5 minutes. The allicin concentration of the top acetone layer and the bottom brine layer was determined to be 2% (w/v) and 0.08% (w/v) respectively.

The acetone layer was then mixed with a 25 liters solution of Acetone/water/acetic acid (65/34/1) in a 100 liters reactor. The solution was then heated at 40 degrees for 6.5 hours. The reaction was monitored by the HPLC ajoene method described above. The reaction mixture was then paper filtered through a 30 cm 113 Whatman paper filter. The liquid was then partitioned against 2×10 liters of pentane to remove non-polar allicin metabolites such as the polysulphides and vinyl dithiins. The filtrate was then reduced under vacuum at 50° C. to remove solvent. The residue and the oil were homogenised with stirring. The residue acetic acid in the liquid was neutralised with the drop wise addition of a concentrated sodium hydroxide solution.

The aqueous liquid was then extracted with 2×5 liters of methyl tert butyl ether. The methyl tert butyl ether extracts were combined then dried with magnesium sulphate. The dried methyl tert butyl ether was then reduced under vacuum at 50° C. A total of 210 g of oil was obtained and the ajoene content was determined to be 50% (w/v) and the E/Z ratio was determined to be 3.1

Example 3

The procedure described in Example 2 was used to produce 30 liters 15,000 ppm allicin solution. The liquid was clarified via centrifuge at 3000 rpm for 45 minutes. The solution was then saturated with 13 Kg of ammonium sulphate. The solution was stirred to ensure saturation; any undissolved salt was removed by filtration. The solution was then extracted with 15 liters of ice-cold acetone. The acetone solution was transferred to an insulated vessel; the temperature of the reactor was dropped to −70° C. with the addition of dry ice. The cold solution was then filtered under vacuum through celite over a paper filter. The filtrate was then dried with magnesium sulphate and filtered again over celite.

The acetone layer was then mixed with a 15 liters solution of acetone/water/acetic acid (65/34/1) in a 100 liters reactor. The solution was then heated at 50° C. for 4 hours. The reaction was monitored by the HPLC ajoene method. The reaction mixture was then paper filtered through a 30 cm 113 Whatman paper filter. The filtrate was then reduced under vacuum at 60° C. to remove solvent. The residue was dissolved in 10 liters of 50% methanol solution. This solution was then washed against 2×5 liters of hexane. The aqueous layer was then extracted with 2.5 liters of dichloromethane. The DCM was dried with magnesium sulphate then reduced.

258 ml of liquid with an ajoene content of 40% w/v was produced.

Example 4

The procedure described in example 1 was used to produce 15 liters of 15,000 ppm allicin solution. The allicin solution was clarified by sedimentation at 4° C. for 24 hours. The solution was then frozen at −10° C. for 48 hours. The frozen block was then shattered with a hammer then pulverized to a fine slush with a domestic blender. The slush wash filtered through a course grade sieve to remove large ice particles. The slush was filtered under vacuum for 3 hours. The liquid/slush was stirred at all times to aid filtering. The temperature was kept bellow 10° C. 6 liters of filtrate were collected and determined to have an allicin content of 30,000 ppm using the HPLC allicin method described above. The filtrate was a viscous sticky solution. The remaining solid slush/ice was left to defrost at room temp for 12 hours producing 9 liters of liquid with an allicin content of 5000 ppm.

The 6 liters of allicin solution was then treated using the same conversion and extraction steps as detailed in Example 1. A total of 250 g of oil were obtained, the ajoene content was determined to be 30% and the E/Z ratio was determined to be. 3:1 by the HPLC method described above.

Example 5

Ajoene was produced as described in Example 1. The ajoene produced was further dried on magnesium sulphate and suspended in olive oil to give an oil macerate containing about 4% ajoene. This concentrate can be further diluted with any suitable edible oil for use to between 100 ppm and 500 ppm depending on the end user and application. This product is stable for a minimum of 2 years when suitably encapsulated and used as a health food supplement or other known applications.

Example 6

10 ml of diallyl disulphide (DADS) were stirred into 100 ml ethanol/water (1:1). 20 grams of potassium peroxymonosulfate (Oxone®) was added slowly over 2 hours, and stirred at below 10° C. until no further reaction was observed. The resultant solution was then filtered, and then extracted with diethyl ether (2×50 ml). The diethyl ether layers were combined and washed with 10% brine solution 2×50 ml. The ether layer was dried with magnesium sulfate then reduced to under vacuum. Removal of the solvent produced a yellow oil of pure allicin better than 90% (expressed as a % of pure material). The pure allicin may then be treated as per Example 1 for conversion to ajoene.

The invention claimed is:
1. A process for preparing ajoene, the process comprising heating an acidic solution comprising an organic solvent and allicin for a sufficient period of time to convert at least a portion of the allicin to ajoene.
2. The process according to claim 1, where the acidic solution comprises the organic solvent, an acid and water.
3. The process according to claim 2, wherein the organic solvent is an alcohol, an ether or a ketone.
4. The process according to claim 3, wherein the organic solvent is acetone, butanol or butanone.
5. The process according to claim 2, wherein an amount of the organic solvent is from about 50 to 70% (v/v) with a remaining portion water.
6. The process according to claim 5, wherein the acid is acetic acid, the organic solvent is acetone, and a remainder is water.
7. The process according to claim 2, further comprising removing the organic solvent to obtain an oily fraction comprising ajoene in an amount of at least or about 30% w/v based on a total volume of the oily fraction.
8. The process according to claim 7, wherein the oily fraction is extracted with an organic polar solvent to remove residual organic solvent and dried to remove residual water.
9. The process according to claim 8, further comprising suspending the oily fraction in edible oil to form an oil macerate containing about 4-5% w/v ajoene based on a total volume of the oil macerate.
10. The process according to claim 9, wherein the edible oil is olive oil.
11. The process according to claim 1, wherein the acidic solution comprises an organic acid or an inorganic acid.
12. The process according to claim 11, wherein the acid has a pKa of less than or about 5.
13. The process according to claim 12, wherein the acid is at least one acid selected from the group consisting of acetic acid, phosphoric acid, sulfuric acid and hydrochloric acid.
14. The process according to claim 13, wherein an amount of the acid in the acidic solution is from about 0.1 to 5% (v/v).
15. The process according to claim 14, wherein the amount of the acid in the acidic solution is from about 0.1 to about 1% (v/v).
16. The process according to claim 1, wherein the heating is at a temperature of from about 30° C. to about 80° C.
17. The process according to claim 16, wherein the temperature is about 40° C. or about 50° C. or about 60° C.
18. The process according to claim 1, wherein a majority of the allicin is converted to ajoene.

19. The process according to claim 18, wherein substantially all of the allicin is converted to ajoene.

20. The process according to claim 1, wherein the acidic solution of the allicin has a pH of from about 3 to about 5, or a pH of from about 3 to less than 5.

21. The process according to claim 1, wherein the acidic solution comprising the allicin is prepared by a process comprising:
   i) mechanically treating a natural plant source of alliinase and simultaneously subjecting the mechanically treated product to centrifugal forces separating a solution comprising alliinase from the natural plant source of alliinase; and
   ii) contacting the solution comprising alliinase source with an aqueous solution of alliin, whereby the alliin is enzymatically converted to allicin by the alliinase, thereby producing an aqueous solution comprising allicin.

22. The process according to claim 21, wherein step (i) is conducted in a centrifugal juicer.

23. The process according to claim 22, wherein step (ii) is carried out simultaneously with at least a part of step (i).

24. The process according to claim 21, wherein after the contacting step the solution comprising the alliin, the alliinase and the allicin is stirred for about 1 to 4 hours, wherein a temperature during stirring is maintainable at about 30° C.

25. The process according to claim 24, wherein the allicin is extracted into an organic solvent after conversion.

26. The process according to claim 25, wherein the organic solvent is an alcohol, an ether or a ketone.

27. The process according to claim 26, wherein the solvent is acetone, butanol or butanone.

28. The process according to claim 25, wherein the organic solvent is the same organic solvent as used in the acidic solution comprising allicin.

29. The process according to claim 28, wherein extraction is carried in a presence of a salt, including sodium chloride.

30. The process according to claim 29, wherein the salt and the organic solvent are added to the solution comprising the allicin with agitation, and the formation of an emulsion during addition of the salt and organic solvent is prevented or minimized.

31. The process according to claim 21, wherein the natural plant source of the alliinase is raw garlic.

32. The process according to claim 31, wherein the raw garlic is in the form of bulbs of cloves peeled and cleaned.

33. The process according to claim 21, further comprising increasing a concentration of the allicin in the aqueous solution of allicin by freeze concentrating the aqueous solution of allicin and thereby increasing the concentration of allicin.

34. The process according to claim 1, wherein the acidic solution comprising the allicin contains at least 5000 ppm allicin.

35. The process according to claim 34, wherein the acidic solution comprising the allicin contains at least 10,000 ppm allicin, or the acidic solution comprising the allicin contains at least 15,000 ppm allicin, or the acidic solution comprising the allicin contains at least 20,000 ppm allicin, or the acidic solution comprising the allicin contains at least 22,000 ppm allicin.

36. The process according to claim 1, wherein the acidic solution comprising the allicin is prepared by a process which comprises oxidizing a solution comprising diallyl disulphide in a presence of potassium peroxomonosulphate at a temperature of from about 0° C. to about 30° C., followed by extraction of the resultant allicin into an organic solvent.

37. The process according to claim 1, further comprising oxidizing a solution comprising diallyl disulphide in a presence of potassium peroxomonosulphate at a temperature of from about 0° C. to about 30° C., followed by extraction of the resultant allicin into an organic solvent.

38. The process according to claim 37, wherein the amount of diallyl disulphide and potassium peroxomonosulphate is sufficient to produce an aqueous solution of allicin having a concentration of from about 5000 ppm to about 22,000 ppm.

39. The process according to claim 38, wherein the temperature is equal to or less than 10° C.

40. The process according to claim 1, wherein ajoene is prepared on a kilogram scale.

* * * * *